US00RE45561E

(19) United States
(12) Reissued Patent
Barralet et al.

(10) Patent Number: US RE45,561 E
(45) Date of Reissued Patent: Jun. 16, 2015

(54) CALCIUM PHOSPHATE BONE CEMENTS

(75) Inventors: Jake Barralet, Montreal (CA); Uwe Gbureck, Mellrichstadt (DE); Roger Thull, Wurzburg (DE); Ulrike Thull, legal representative, Bassersdorf (CH)

(73) Assignee: Ortus Medical Limited (GB)

(21) Appl. No.: 12/985,939

(22) Filed: Jan. 6, 2011

Related U.S. Patent Documents

Reissue of:
(64) Patent No.: 7,473,312
Issued: Jan. 6, 2009
Appl. No.: 10/557,833
PCT Filed: May 19, 2004
PCT No.: PCT/GB2004/002179
§ 371 (c)(1),
(2), (4) Date: Nov. 22, 2005
PCT Pub. No.: WO2004/103419
PCT Pub. Date: Dec. 2, 2004

(30) Foreign Application Priority Data

May 23, 2003 (GB) ..... 0311846.0

(51) Int. Cl.
*C04B 12/02* (2006.01)
*A61L 24/02* (2006.01)
*A61L 24/00* (2006.01)
*A61L 27/42* (2006.01)

(52) U.S. Cl.
CPC ..... *A61L 24/0063* (2013.01); *C04B 12/02* (2013.01); *A61L 27/425* (2013.01)

(58) Field of Classification Search
USPC ..... 106/690, 691, 692
See application file for complete search history.

(56) References Cited

U.S. PATENT DOCUMENTS 6,425,949 B1 7/2002 Lemaitre et al. ..... 106/35
6,723,334 B1 * 4/2004 McGee et al. ..... 424/423
2007/0221093 A1 * 9/2007 Erdrich et al. ..... 106/35

OTHER PUBLICATIONS

Sarda et al., "Kinetic study of citric acid influence on calcium phosphate bone cements as water-reducing agent", J. Biomed. Mater. Res., Sep. 2002, vol. 61, No. 4, pp. 653-659.*
Chen, "Physical properties of apatite bone cement", Journal of Biomedical Engineering, Mar. 2000, abstract only.*
Chen et al., "Study on the mechanical properties of Hydroxyapatite bone cement", Chinese Journal of Clinical Rehabilitation, 2004, abstract only.*
Gbureck U et al: "Surface Properties of Calcium Phosphate Particles for Self Setting Bone Cements" Biomolecular Engineering, Elsevier, New York, NY, US, vol. 19, No. 2-6 Aug. 2002, pp. 51-55, XP004378070 ISSN: 1389-0344, the whole document, p. 51, right-hand column.
Bohner M et al: "Effects fo Sulfate, Pyrophosphate, and Citrate Ions on the Physicochemical Properties of Cements Made of Beta-Tricalcium Phosphate-Phosphoric Acid-Water Mixtures" Journal of the American Ceramic Society, American Ceramic Society, Columbus, US, vol. 79, No. 6, Jun. 1, 1996, pp. 1427-1434, XP000596067, ISSN: 0002-7820, figure 9.
Otsuka M et al: "Particle Size Effect of Metastable Calcium Phosphates on Crushing Strength of Self-Setting Bioactive Calcium Phosphate Cement" Chemical and Pharmaceutical Bulletin, Pharmaceutical Society of Japan, Tokyo, JP, vol. 41, No. 11 Nov. 1, 1993, pp. 2055-2057, XP009001135, ISSN: 0009-2363, figure 5; table II.
Gbureck U et al: "Ionic Modification of Calcium Phosphate Cement Viscosity. Part I: Hypodermic Injection and Strength Improvement of Apatite Cement" Biomaterials, Elsevier Science Publishers BV., Barking, GB, vol. 25, No. 11. Nov. 6, 2003, pp. 2187-2195, XP00485137, ISSN: 0142-9612, Online publication date, the whole document.
Barralet J E et al: "Ionic Modification of Calcium Phosphate Cement Viscosity. Part II: Hypodermic Injection and Strength Improvement of Brushite Cement" Biomaterials, Elsevier Science Publishers BV., Barking, GB, vol. 25, No. 11, Nov. 19, 2003, pp. 2197-2203, XP004485138, ISSN: 0142-9612, Online publication date, the whole document.
Fernandez Enrique et al: "Kinetic Study of Citric Acid Influence on Calcium Phosphate Bone Cements as Water-Reducing Agent" J. Biomed. Mater. Res.; Journal of Biomedical Materials Research Sep. 15, 2002, vol. 61, No. 4 Sep. 15, 2002, pp. 653-659, XP002301639, cited in the application, abstract, figures 1, 2, p. 657, righ-hand column, paragraph 2-paragraph 3.
Database Medline 'Online!, US National Library of Medicine (NLM), Bethesda, MD, US; Mar. 2000, Chen D: "Physical Properties of Apatite Bone Cement!" XP002301640 Database Accession No. NLM10879182 Abstract & Sheng Wu Yi Xue Gong Cheng Xue Za Zhi = Journal of Biomedical Egineering = Shengw Yixue Gongchengxue Zazhi, Mar. 2000, vol. 17, No. 1, Mar. 2000, pp. 13-15, 18, ISSN: 1001-5515.
Database Embase 'Online! Elsevier Science Publishers, Amsterdam, NL, 2004, Chen D-M et al: "Study on the Mechanical Properties of Hydroxyapatite Bone Cement" XP002301641, Database accession No. EMB-2004217475, Abstract & Chinese Journal of Clinical Rehabilitation 2004, China, vol. 8, No. 8, 2004, pp. 1589-1591, ISSN: 1671-5926.

* cited by examiner

*Primary Examiner* — Elizabeth Wood
(74) *Attorney, Agent, or Firm* — Fish & Richardson P.C.

(57) ABSTRACT

In a first aspect, the present invention discloses a self setting calcium phosphate cement comprising:—(i) a powdered component, said powdered component having an average particle size $d_{50}$ of less than 15 μm, and (ii) a calcium phosphate based powder, said powder having an average particle size $d_{50}$ greater than that of the powdered component, said powdered component and said calcium phosphate based powder being suspended in water containing a dissolved zeta potential increasing additive in sufficient quantity to increase the zeta potential of the suspended particles to at least 30 mV, and wherein the zeta potential increasing additive is chosen to be compatible with the setting pH of the same calcium phosphate cement without the zeta potential increasing additive. In a second aspect, the invention discloses a shelf-stable acidic setting cement powder comprising:—(i) a calcium phosphate based powder, and (ii) a powdered compound which, upon addition of water to form a cement paste, retards the cement setting reaction or increases the zeta potential of the resultant suspended particles to at least −30 mV.

1 Claim, 5 Drawing Sheets

CALCIUM PHOSPHATE BONE CEMENTS

Figure 1:
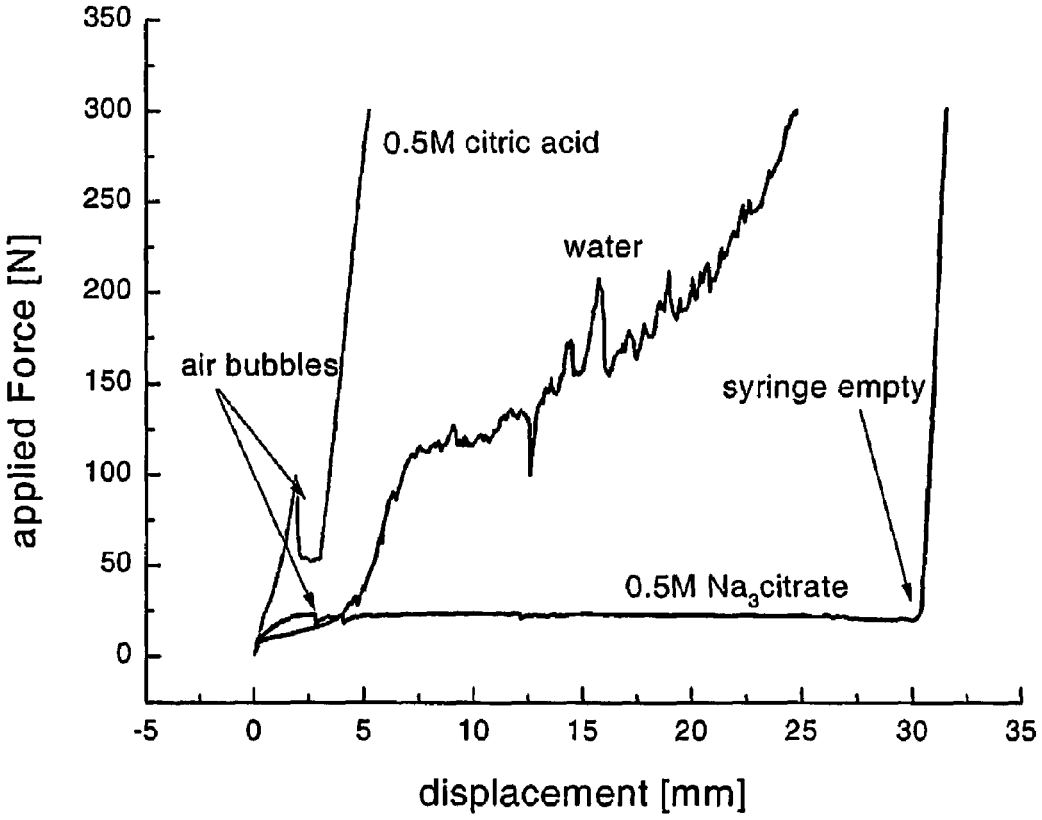

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

The present invention in one aspect relates to an improved self-setting calcium phosphate cement which is injectable and mechanically strong when set. In a second aspect the invention relates to a shelf-stable acidic setting cement powder.

Clinically, the main application of self-setting calcium phosphate cements (CPC) is currently in cranio-and maxillofacial surgery for the reconstruction of bone defects, due to their ease of use, clinical performance and conformability. The location of these defect sites is chosen so that little loading of the implant occurs, since these materials are both weak and brittle compared to the bone they replace. Compressive strengths of CPC reported in literature are in the range of 20-83 MPa, dependent on the composition and pretreatment of the materials, while the strength of cortical bone is up to about 170 MPa. A broadening of the indications for which CPC can be used, for example in the field of upper spine surgery (vertebroplasty), may require a higher strength material. Additionally a cement paste that had high strength in addition to being of sufficiently low viscosity as to be applied by minimal invasive injectable materials, would further widen applications to include indications not freely accessible by open surgery.

Often when unmodified CPC, consisting of calcium phosphate particles and water containing dissolved phosphate/hydrogen phosphate ions as liquid phase, is delivered through a narrow bore needle or cannula, a filter-pressing phenomenon can occur leading to a separation of liquid and solid phases. Injectable cements can be obtained by decreasing the powder to liquid ratio (P/L ratio), but this has a detrimental effect on the mechanical properties due to a higher porosity of the hardened cement matrix. In an attempt to improve rheological properties, the influence of several additives to the liquid phase, such as: lactic acid, glycerol, chitosan, citric acid or soluble polymers, on the injectability of calcium phosphate cements has been studied by several authors (Leroux L, et. al.: Effects of various adjuvant (lactic acid, glycerol and chitosan) on the injectability of a calcium phosphate cement. Bone 1999; 25(2): 31-34. and Ginebra M P, et. al.: Mechanical and rheological improvement of a calcium phosphate cement by the addition of a polymeric drug. J Biomed Mater Res 2001; 57(1): 113-118).

Several authors have investigated the influence of citric acid on the properties of calcium phosphate cements and the reaction kinetics of hydroxyapatite formation (Sarda S, et. al.: Kinetic effect of citric acid influence on calcium phosphate bone cements as water reducing agent, J Biomed Mater Res 61: 652-659, 2002). Citric acid retards the formation of hydroxyapatite as was shown for phase pure α-TCP as well as for TTCP/DCPD cement systems. The setting reaction to HA is retarded, probably because of adsorption of the citrate ions onto both reactant and product phases and a low pH value of the cement paste during hardening. In contrast to acetate ions, the level of super saturation, necessary for precipitation of HA from the liquid, increases in the presence of citrate ions from 10.93 to 11.73 (Van der Houwen, JAM, et al.: The application of calcium phosphate precipitation chemistry to phosphorous recovery: the influence of organic legends, Environmental Technology, 2001; 22: 1325-1335). In some cases, citric acid has been shown to increase the injectability of cement pastes at lower levels of the acid but large gains in strength have not been reported as a consequence of the reduced water content of these formulations.

It is an object of the present invention in a first aspect to provide an improved self setting calcium phosphate cement which preferably has improved mechanical properties when set and which is preferably of sufficiently low viscosity to be injectable.

According to a first aspect of the present invention there is provided a self setting calcium phosphate cement comprising:

(i) a powdered component, said powdered component having an average particle size $d_{50}$ of less than 15 μm, and (ii) a calcium phosphate based powder, said powder having an average particle size $d_{50}$ greater than that of the powdered component, said powdered component and said calcium phosphate based powder being suspended in water containing a dissolved zeta potential increasing additive in sufficient quantity to increase the zeta potential of the suspended particles to at least −30 mV, and wherein the zeta potential increasing additive is chosen to be compatible with the setting pH of the same calcium phosphate cement without the zeta potential increasing additive.

Preferably, the $d_{50}$ of the calcium phosphate based powder is from about 1.5 to about 10 times greater than the $d_{50}$ of the powdered component.

Preferably, the zeta potential increasing additive is an oligocarboxylic acid compound.

It will be understood that certain calcium phosphate based cements set at an approximately neutral pH, in which case the oligocarboxylic acid compound is an appropriate salt of the carboxylic acid. Suitable salts include group I or group II metal salts (e.g. sodium, potassium or calcium), ammonium salts and mixed salts. For the avoidance of doubt, said salts are not limited to neutral salts, and may include partial salts. Other calcium phosphate based cements set at acidic pH, in which case the oligocarboxylic acid compound is the oligocarboxylic acid itself.

Preferably, said oligocarboxylic acid compound has two or three carboxyl groups. Preferably, said oligocarboxylic acid compound has one or more hydroxyl groups.

Preferred oligocarboxylic acids compounds are citric acid, tartaric acid and malic acid, and their salts, with trisodium citrate and disodium tartrate being particularly preferred for neutral setting cements.

Preferably, the zeta potential increasing additive is in sufficient quantity to increase the zeta potential of the calcium phosphate particles to at least −40 and preferably at least −50 mV.

Preferably, the zeta potential increasing additive is present in an amount of from 0.01 to 2 Mol per liter of water, more preferably 0.1 to 1 Mol per liter and most preferably 0.2 to 1 M per liter.

Preferably, the powdered component has a $d_{50}$ of no more than 10 μm, more preferably no more than 5 μm and possibly as low as 1 μm or less. Preferably, the powdered component is a carbonate, silicate, nitrate, oxide or sulphate and/or a salt of calcium, zirconium, aluminum, titanium or silicon, or mixtures thereof. More preferably, the powdered component is calcium phosphate based, for example it may be calcium phosphate (hydrated or anhydrous), dicalcium phosphate anhydrous, dicalcium phosphate dihydrate, α-tricalcium phosphate, β-tricalcium phosphate, tetracalcium phosphate, hydroxyapatite, or octacalcium phosphate or substituted (e.g. potassium, silicon, sodium, carbonate, sulphate etc.) forms thereof. Alternatively, the powdered component may be any other biocompatible ceramic material such as calcium carbonate, calcium sulphate, zirconium oxide or titanium oxide or mixtures thereof.

Preferably, the calcium phosphate based material has a $d_{50}$ of at least 3 μm. Preferably, the calcium phosphate based material (which may be in any convenient state for example crystalline, nanocrystalline, amorphous or mechanically activated) is tetracalcium phosphate, α- or β-tricalcium phosphate, hydroxyapatite, monocalcium phosphate monohydrate, monocalcium phosphate anhydrous or mixtures thereof.

Preferably, said calcium phosphate based material is mechanically activated. More preferably, said calcium phosphate based material is mechanically activated α- or β-tricalcium phosphate.

Preferably, the volume ratio of the calcium phosphate based powder to the powdered component is in the range of from 50:40 to 95:5. More preferably, the powdered component is present at no more than 40% and even more preferably no more than 30% based on the volume of calcium phosphate based powder. A particularly preferred range for the powdered component is 10 to 25% by volume of the calcium phosphate based powder.

The inventors have discovered that the combination of the bimodal particle distribution and the presence of the zeta potential increasing compound have a considerable effect on the viscosity of the resulting calcium phosphate cement. As such, much higher powder to liquid ratios can be achieved whilst maintaining injectability of the cement.

Furthermore, the cements of the present invention may be re-molded or shaped after pre-compression, to give either high strength cements which can be applied clinically in the absence of applied pressure, or high strength near-net-shape implants.

It will be understood that the invention also resides in cement powders having the above-described bimodal particle distribution.

According to a second aspect of the present invention, there is provided a shelf-stable acidic setting cement powder comprising:—

(i) a calcium phosphate based powder, and (ii) a powdered compound which, upon addition of water to form a cement paste, retards the cement setting reaction or increases the zeta potential of the resultant suspended particles to at least −30 mV As used herein, a cement powder is to be regarded as "shelf stable" if, when formed into a cement, the cement will set after the powder has been stored for a predetermined period of time. Preferably, the cements of the present invention are shelf stable for at least 7 days, more preferably 21 days and most preferably 6 months or more.

The powdered compound may be present at up to 50 mol % of the cement powder, preferably up to 20 mol % more preferably from about 5 to 15 mol % and most preferably about 10 wt %.

Preferably, said calcium phosphate based powder comprises β-TCP or α-TCP.

Preferably the powdered component is selected from an oligocarboxylic acid compound and a pyrophosphate salt (e.g. calcium pyrophosphate). Preferably, the oligocarboxylic acid compound has two or three carboxyl groups. More preferably, the oligocarboxylic acid compound is selected from citric acid, tartaric acid and malic acid.

The oligocarboxylic acid compound may be a salt of the carboxylic acid (e.g. a group I or group II metal salt an ammonium salt or a mixed salt) but is preferably the free acid.

It will be understood that the cement powders of the second aspect may be powder mixtures having the bimodal particle distribution of the first aspect and may be formed into cements using an aqueous solution of the zeta potential increasing additives of the first aspect.

The present invention will be further described by way of example only with reference to the accompanying drawings in which:—

Figure 2:
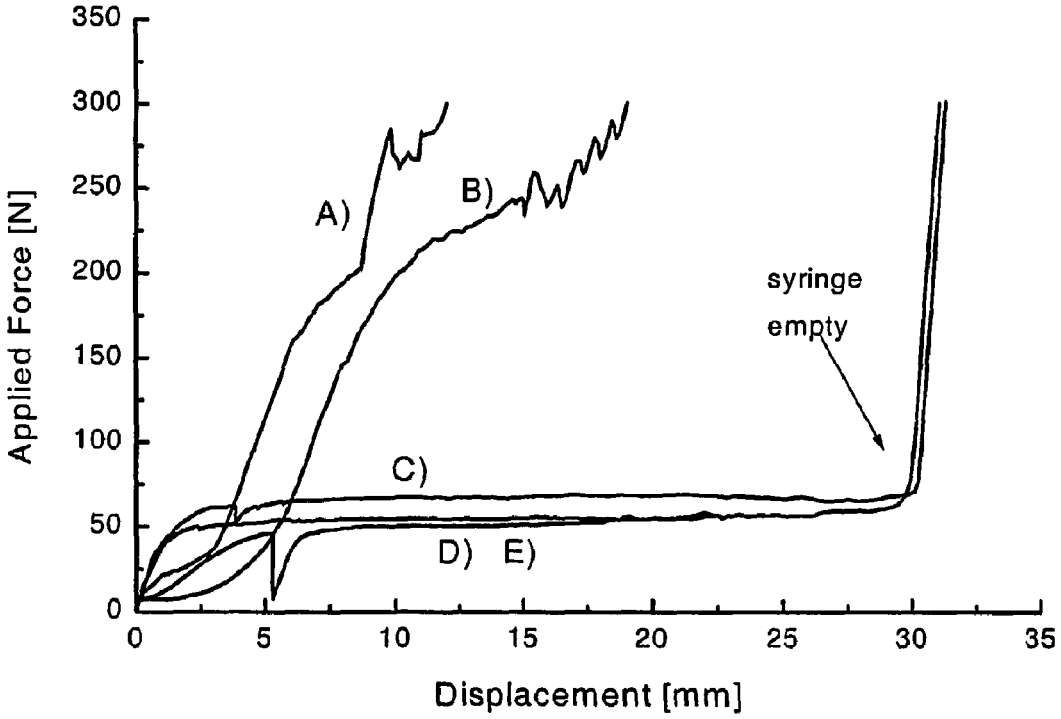
Figure 3:
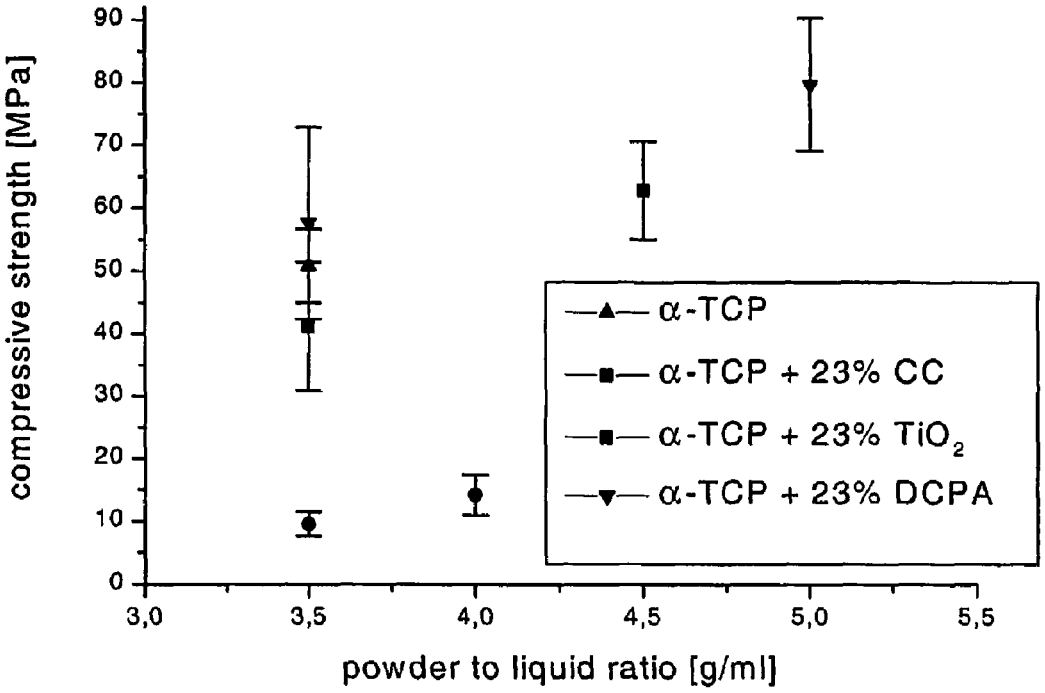
Figure 4:
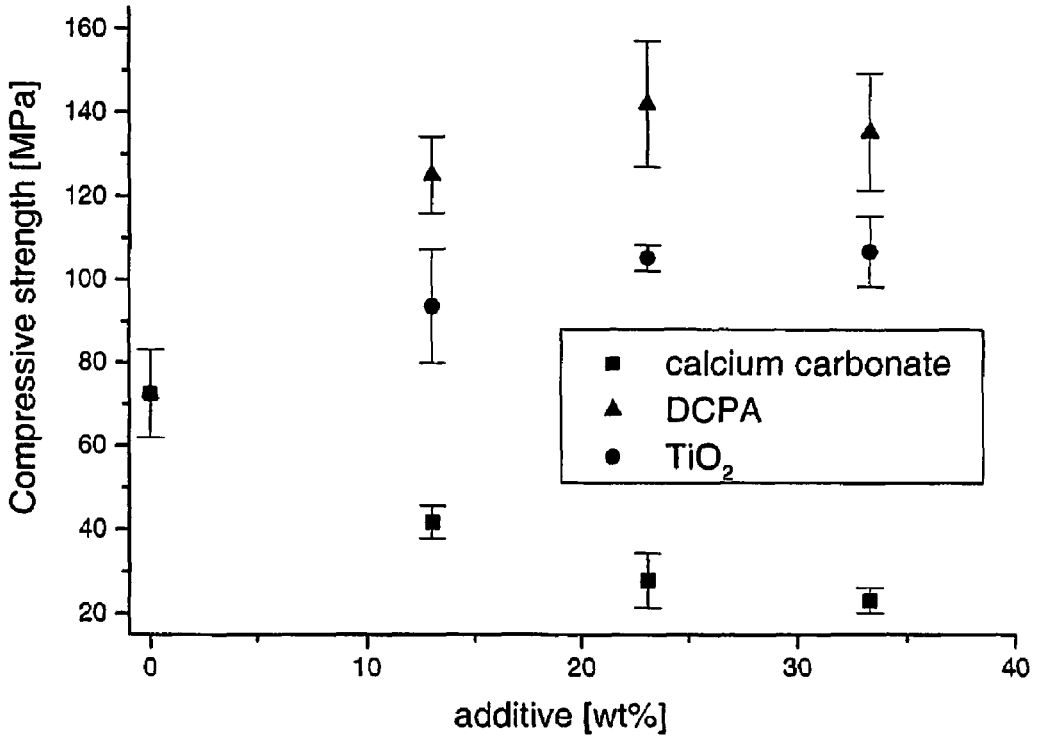
Figure 5:
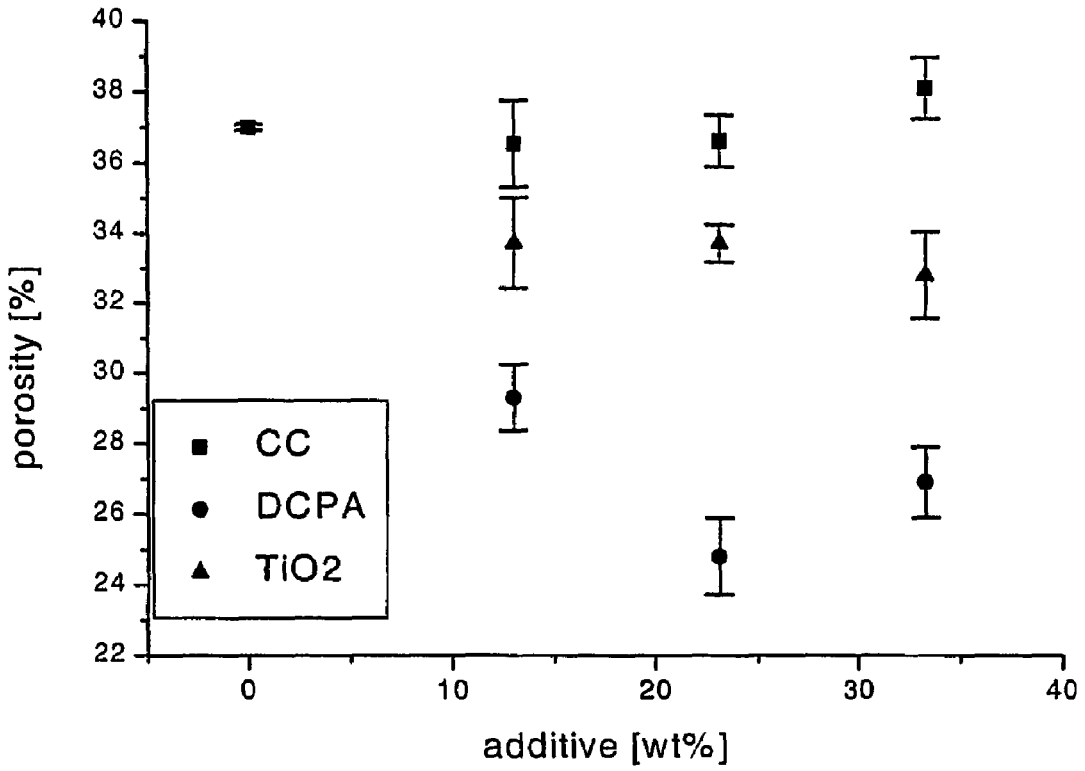

FIGS. 1 and 2 are plots of applied force against displacement to show injectability of various cement compositions, FIG. 3 is a plot of compressive strength of encompassed α-TCP cements at P:L 3.5 and at P:Lmax formed with 0.5M $Na_3$Citrate/2.5% $Na_2HPO_4$ solution, FIG. 4 is a plot of compressive strengths of pre-compacted α-TCP based cements with a P:L of 3.5 after 7 d setting at 37° C., and FIG. 5 shows porosities of compacted cement samples for different additive filler content.

CPC can be considered as a high viscosity ceramic powder suspension. The basic principle of the present invention is the adjustment of a surface charge of the cement particle surface in the liquid phase (zeta-potential). A high zeta-potential improves the dispersion of the fine particles in the micron to sub-micron range as a result of the mutual repulsion of particles in the liquid phase and minimizes therefore the attractive interparticulate forces. For cements with a bimodal particle size distribution as claimed, the high surface charge of the particles allows the de-agglomeration of the fine particles in the liquid phase. These de-agglomerated fine particles can then fill the space between a dense packing of the coarser particles, minimizing the required liquid for cement paste formation and the resulting porosity and therefore maximizing the mechanical strength of the hardened cement matrix. Zeta-potential may be altered by adding multiple charged ions to the liquid phase, which can lead to an increase of the charge density of the particle surface by adsorption on the solid/liquid interface. The main requirements for additives to CPC for implantation are non-toxicity as well as lack of detrimental effect on mechanical properties e.g. due to excessive inhibition of the cement setting reaction. Particularly useful additives for increasing the zeta-potential within CPC are sodium (and calcium) salts of citric acid.

A. TTCP/DCPA Cement

Cement preparation: TTCP (tetracalcium phosphate) was prepared by sintering an equimolar mixture of DCPA (dicalcium phosphate anhydrous) (Baker) and calcium carbonate (Baker) at 1500° C. for 18 h followed by quenching in air, followed by milling in agate jars to a $d_{50}$ of 15 μm. DCPA was milled in 96% ethanol by means of a ball mill for 24 h to a $d_{50}$ of 0.7 μm. TTCP and DCPA were mixed at a nearly equimolar ratio (0.91), weight ratio 7:3 in a ball mill for 1 h. 0.97 weight % of dry sodium phosphate accelerator was mixed with the cement to adjust the initial setting time according to the Gilmore-needle test to about 5 min at 37° C.

Specimen Preparation: Cement cylinders with an aspect ratio of 2:1 (6 mm diameter×12 mm length) were fabricated with powder to liquid mass ratios of between 2.7-5. The cement pastes were biaxially compressed up to 200 MPa for 5 s. The specimens were removed from the moulds after 2 h setting and stored in water at 37° C. for an additional 22 h prior to testing.

Compressive testing: Strengths (n=6) were measured at a crosshead speed of 1 mm/min using a static mechanical testing machine Zwick 1440 (Zwick, Ulm, Germany) with a 5 kN load cell. Samples with strengths over 160 MPa were tested on an Instron 1185 with a 100 kN load cell.

Injectability

10 g of CPC powder were mixed with water or 500 mM trisodium citrate solution at L mass ratios of between 3.3 and 5 on a glass slab. The cement paste was transferred into a 10 ml syringe by means of a spatula: The paste was extruded through a 1.1 mm×30 mm needle using a mechanical testing machine (Zwick 1440) at cross-head speed of 20 mm/min and a maximum force of 300 N. This force was selected since this was determined to be the maximum force that could be applied manually. The amount of cement remaining within the syringe was weighed and the injectability (I) was calculated according to:

$$I\ (\%) = \frac{\text{Mass of cement paste injected through needle} \times 100}{\text{Original mass of cement paste in syringe}}$$

COMPARATIVE EXAMPLES

The liquid phase was either water, an aqueous solution of citric acid (500 mM) or an aqueous solution of sodium acetate.

EXAMPLES

The liquid phase was an aqueous solution of trisodium citrate at concentrations of 100 mM to 1 M, or disodium tartrate at a concentration of 500 mM.

1. Trisodium Citrate Containing Solutions

The compressive strengths of the cement samples precompacted to 2.7 MPa are tabulated in Table 1 below. At a P/L ratio of 3.3 it can be seen that the values for the trisodium citrate samples are higher than for the comparative water and citric acid samples. The effect is even more marked at higher levels of sodium citrate, with the strengths being 50-60% higher at 500 mM trisodium citrate. The effect can be explained mechanistically by a decrease of the porosity of the hardened cement matrix.

TABLE 1

| | Compressive strength [MPa] | | |
|---|---|---|---|
| Liquid | P/L = 3.3 | P/L = 4 | P/L = 5 |
| water | 62.5 ± 5.0 | 51.6 ± 11.3 | 30.1 ± 10.7 |
| 100 mM $Na_3$citrate | 77.3 ± 8.4 | 78.9 ± 9.7 | 77.1 ± 7.2 |
| 200 mM $Na_3$citrate | 87.4 ± 11.7 | 90.0 ± 6.6 | 93.4 ± 9.6 |
| 500 mM $Na_3$citrate | 102.4 ± 7.5 | 108.7 ± 18.7 | 108.8 ± 13.0 |
| 750 mM $Na_3$Citrate | 101.2 ± 13.3 | — | — |
| 1 M $Na_3$Citrate | 98.9 ± 14.0 | — | — |
| 500 mM Citric Acid | 67.1 ± 9.3 | — | 26.2 ± 6.1 |

As might be expected, as the P/L ratio increases, the strengths of the water and citric acid cements decreases, primary due to the difficulty in mixing such a dry paste causing poor sample quality. In contrast, the strength of the trisodium citrate samples was relatively insensitive to the P/L ratio.

Furthermore, the use of trisodium citrate solutions as liquid phase in different concentrations (0.1-1 mol/l) results in a decrease of the macroscopically observable viscosity of the cement paste and therefore permits improved injectability.

Referring to FIG. 1, injectability of cements mixed with 0.5M trisodium citrate solution (P/L of 3.3) were compared with injectability of cements having water or citric acid (0.5M) as the liquid phase. The applied force increased at the beginning of the injection and reached a constant level after several mm displacement of the syringe, disrupted only in part by a sudden decrease of the pressure when air bubbles were pressed out through the needle. After about 25-30 mm displacement the applied forces strongly increase up to the limit of 300N since no further paste remained in the syringe. In contrast, water and 0.5M citric acid solution containing pastes only had injectabilities of 60% and 13% respectively (P/L 3.3, max force 300N). For both liquids a continuous increase of the injection forces were obtained. The applied forces for injecting cement pastes with sodium citrate solution increase with cross-head speed; an average speed of 20 mm/min (about 90 s for injecting the whole cement paste) requires a force of 22-24 N at P/L=3.3 compared to 60 N at a speed of 50 mm/min. Higher P/L mixes (up to 4.5) were still injectable (>90%), but required higher forces, typically 90-120 N.

The reason for the observable effects of an increased injectability and a mechanical reinforcement is the highly charged particle surface (zeta-potential) of the calcium phosphate particle when trisodium citrate is used as liquid. The zeta-potentials of DCPA and TTCP has been reported previously as −15 mV (TTCP) and −18 mV (DCPA) in pure water. Using trisodium citrate solution the particle surfaces were highly charged due to the adsorption of citrate ions with zeta-potentials of about −50 to −55 mV. This increase of the zeta-potential leads to a much lower viscosity of the cement paste due to a decrease of the attractive interparticulate forces by an electrostatic mutual repulsion of the particles in combination with a bimodal particle size distribution of the cement.

HA cement mixed with water, sodium citrate and citric acid solutions (P/L ratio 3.3) were compacted at 2.7, 9.0, 36, 50 and 200 MPa. Compressive strength, density and phase composition were determined after storage in water at 37° C. after 24 hours. Table 2 shows the effect of compaction pressure and liquid composition on the mechanical properties and degree of conversion of cements mixed at a P:L ratio of 3.3.

TABLE 2

| Liquid | Compaction Pressure (MPa) | Compressive Strength (MPa) | wt % HA |
|---|---|---|---|
| Water | 2.7 | 62.5 ± 5.0 | 79.96 |
| Water | 9 | 83.4 ± 11.4 | 74.84 |
| Water | 36 | 106.8 ± 11.0 | 72.37 |
| Water | 50 | 113.2 ± 16.0 | 77.93 |
| Water | 200 | 118 ± 16.0 | 27.58 |
| 100 mM $Na_3C$ | 2.7 | 77.3 ± 8.4 | 77.19 |
| 200 mM $Na_3C$ | 2.7 | 87.4 ± 11.7 | 76.6 |
| 500 mM $Na_3C$ | 2.7 | 102.40 ± 7.5 | 78.67 |
| 500 mM $Na_3C$ | 9 | 131.3 ± 8.8 | 78.47 |
| 500 mM $Na_3C$ | 36 | 154.4 ± 14.4 | 78.45 |
| 500 mM $Na_3C$ | 50 | 153.6 ± 19.3 | 73.58 |
| 500 mM $Na_3C$ | 200 | 184.0 ± 19.3 | 38.62 |
| 500 mM CA | 2.7 | 22.3 ± 6.4 | 61.49 |
| (48 hrs) | | 67.1 ± 9.3 | (66.67) |
| 500 mM CA | 9 | 21.0 ± 3.6 | 67.59 |
| (48 hrs) | | 86.9 ± 11.1 | 77.50 |
| 500 mM CA | 50 | 29.4 ± 4.3 | 72.13 |
| (48 hrs) | | 115.9 ± 9.7 | 80.72 |

CA = citric acid, $Na_3C$ = trisodium citrate

It was found that by compacting cements made with sodium citrate biaxially to 200 MPa, very high strength materials were produced (184 MPa) despite the extent of reaction being limited, whereas water and citric acid only yielded cements with 116-118 MPa. After 24 hr setting cement made with citric acid was initially very weak (20-30 MPa) and this increased after a further 24 hours to similar levels achieved using water.

Cement mixes, (powder: liquid ratio 3.3 g/ml) containing either water, 500 mM citric acid or sodium citrate that were manually pressed into cylindrical moulds under finger pressure, (estimated from load cell measurements to be ~1.5 MPa) were investigated. The use of sodium citrate had a remarkable strength improvement effect over the use of water (101.2±13.7 and 33.1±11.9 MPa respectively). The low and variable strengths of the water mixed cements was as a result of poor specimen quality due to difficulties in handling and compacting the thick paste, sodium citrate containing mixes however were a viscous liquid. In order to determine whether high strength near net shape cement implants could be made by pre-compaction, rectangular prisms (aspect ratio 2:1) were cut with a scalpel from unset cement cylinders made with 500 mM sodium citrate compacted to 2.7 MPa. After 24 hours they were found to have wet compressive strengths of 97.4±8.6 MPa. In order to determine whether a moldable system could be generated, the same cement formulation was compacted to 2 MPa and removed from the die. The cement paste was then transferred into cylindrical moulds by spatula and allowed to set before removal and storage in water for 24 hours. These cements had wet compressive strengths of 88.6±6.3 MPa. This demonstrates the potential of using a precompaction stage in a delivery system of sodium citrate containing CPC to generate high strength cement pastes that can be applied clinically in the absence of applied pressure.

By using a compaction pressure of 200 MPa it was possible to fabricate cements with a mean wet strength in excess of 180 MPa. This is near to the upper strength range of cortical bone and demonstrates that this cement system may be capable of being used in some load bearing applications.

Even without precompaction, strength values are higher using sodium citrate (500 mM) than using water (Table 3). Furthermore, the lowering of viscosity enables higher workable P/L ratios to be obtained.

TABLE 3

| | P/L | | | | | |
|---|---|---|---|---|---|---|
| | 2.0 | 2.7 | 3.3 | 4.0 | 4.5 | 5.0 |
| 0.5M sodium citrate | 8.7 ± 0.7 | 28.1 ± 1.2 | 36.1 ± 4.1 | 50.5 ± 6.0 | 57.7 ± 10.8 | 67.1 ± 6.1 |
| water | 4.8 ± 1.2 | — | 17.6 ± 2.87 | UNWORKABLE | | |

2. Disodium Tartrate Containing Solutions

The scope of the invention was further explored by making TTCP/DCPA cements (as described above) using a disodium tartrate solution (500 mM) instead of trisodium citrate. A similar strength sodium acetate solution was used for comparison.

The effective surface charges of the TTCP, DCPA and precipitated HA particles in contact with an aqueous electrolyte were determined from zeta-potential measurement. Analysis was performed on a Zeta-Sizer 3000 (Malvern Instruments) in double distilled water and various 50 mM electrolytes. Measurements were performed 10 times and the average potential and the standard deviation were calculated.

As can be seen from Table 4 below, the zeta potentials obtained for the starting calcium phosphates and the resultant hydroxyapatite using disodium tartrate were significantly higher than when using sodium acetate.

TABLE 4

Zeta-Potentials of cement components (TTCP, DCPA) in different electrolytes (0.05 mol/1)

| | Zeta-Potential [mV] | |
|---|---|---|
| | $Na_2$ Tartrate | Na Acetate |
| DCPA | −41.7 +/− 2.1 | −35.4 +/− 0.7 |
| TTCP | −40.9 +/− 2.2 | −28.9 +/− 2.6 |
| HA precip. | −40.5 +/− 1.4 | −13.3 +/− 1.7 |

Compressive strengths were measured (after 24 hrs setting at 37° C. following pre-compression at 2.7 MPa). As can be seen in Table 5 below, the disodium tartrate gave significantly greater (more than double) strength values than sodium acetate.

TABLE 5

Mechanical strengths of TTCP/DCPA cement at various P/L ratios and different compositions of the liquid phase

| | Compressive strength [MPa] | |
|---|---|---|
| Liquid | P/L = 3.3 | P/L = 4 |
| 0.5 mol/l Na Acetate | 45.7 +/− 3.9 | 42.8 +/− 5.7 |
| 0.5 mol/l $Na_2$Tartrate | 96.4 +/− 10.2 | 86.9 +/− 8.4 |

B1. Mechanically Activated α-Tricalcium Phosphate Cements (MaαT)

Cement Preparation

α-TCP was synthesized by heating a mixture of monetize (DCPA; Mallinckrodt Baker, Griesham, Germany) and calcium carbonate (CC; Merck, Darmstadt, Germany) to 1400° C. for 5 h followed by quenching to room temperature in a desiccator. The product consisted of phase pure and highly crystalline α-TCP as verified by X-ray diffraction (XRD). The sintered cake was crushed with a pestle and mortar and passed through a 355 μm sieve. Milling of α-TCP was performed in a planetary ball mill (PM400 Retsch, Germany) at 200 rpm with 500 ml agate jars, 4 agate balls (30 mm) and a load of 75 g α-TCP per jar for 4 hours and 1 hour to give a mechanically activated powder having a $d_{50}$ of 7.1 μm or 6.99 μm respectively. DCPA (Baker, Griesheim, Germany) and CC (Merck, Darmstadt, Germany) were ground in ethanol for up to 24 h, followed by drying in vacuum at 60° C. Commercial $TiO_2$ (retile, Merck) was used as received. Particle size distributions were determined using laser particle size analysis (L300, Horiba, Kyoto, Japan). 100 mg of the powder particles were suspended in 200 ml isopropanol and dispersed by applying ultrasound for 15 min. The effective surface charges of the powders in contact with an aqueous electrolyte were determined from zeta-potential measurement. Analyses were performed on a Zeta-Sizer 3000 (Malvern Instruments) in double distilled water and various 50 mM electrolytes. Measurements were performed ten times and the average potential and the standard deviation were calculated.

The other cement components were added and mixed in a coffee grinder for approximately 20 to 30 seconds. Cement pastes were produced by the mixture of powder and either 2.5 wt % $Na_2HPO_4$ or 2.5 wt % $Na_2HPO_4$/0.5M sodium citrate solution. Firstly, setting experiments were performed to obtain the maximum powder to liquid (P:L) ratio for a workable cement paste. The initial setting times of the cements were measured in a humidity chamber at 37° C. and >90% humidity using the Gilmore needle test with a needle of 113.98 g and 2.117 mm diameter according to ASTM standard C266-99.

Samples for mechanical testing were prepared by mixing 800 mg of powder with the required liquid volume in a nitride rubber mixing container on a vibratory shaker for 15 s. The cement paste was transferred in stainless steel moulds (6 mm in diameter), both ends were closed with suitable stainless steel plungers and pre-compressed by means of a cantilever device described in the literature (Chow L C et. al: Diametric tensile strength and compressive strength of a calcium phosphate cement: effect of applied pressure. J Biomed Mater Res (Appl. Biomater.) 2000; 53: 511-517) at a pressure of 9 MPa for 5 s, followed by a constant load of 0.7 MPa for 2 h. Wet samples (n=6 per condition) with an aspect ratio of 2:1 were tested as described above.

The strut densities of the cement, i.e. the densities of the solid cement products were found using helium pycnometry (Accupyc 1330, Micromeritics, UK). The average densities of three cement samples were calculated using ten purges and ten measurements. These data combined with mass and dimension measurements enabled calculation of relative porosity of the cement. Specimen preparation and compressive strength testing was carried out as described above (pre-compression of samples was at 9 MPa).

The results are shown in Table 6 below, from which it can be seen that the incorporation of DCPA or MaβT to provide a bimodal particle distribution and trisodium citrate to increase the zeta potential resulted in a cement having a higher compressive strength.

TABLE 6

Compressive strengths of MaαT

| Composition | Liquid | P/L | CS [MPa] |
|---|---|---|---|
| MaαT[1] | 2.5 $Na_2HPO_4$ | 2.5 | 82.0 +/− 8.3 |
| MaαT[1], 15% DCPA (0.7 μm) | 0.5 M $Na_3$citrate 2.5 $Na_2HPO_4$ | 4.0 | 114.0 +/− 15.3 |
| MaαT[1], 30% DCPA (0.7 μm) | 0.5 M $Na_3$citrate 2.5 $Na_2HPO_4$ | 4.0 | 114.5 +/− 26.7 |
| MaαT[2] | 2.5 $Na_2HPO_4$ | 2.5 | 74.5 +/− 13.6 |
| MaαT[2], 30% MaβT[3] | 0.5 M $Na_3$citrate 2.5 $Na_2HPO_4$ | 3.6 | 93.3 +/− 16.1 |

[1]Dry ground for 4 hours ($d_{50}$ 7.1 μm)
[2]Wet ground for 1 hour ($d_{50}$ 6.99 μm)
[3]MaβT = mechanically activated II-TCP, wet ground in ethanol to give a powder having a $d_{50}$ of 3 μm.

B2. Mechanically Activated α-Tricalcium Phosphate Cements (MaαT)

Cement Preparation

As described above for B1.

X-ray diffraction patterns of set cements were recorded on a diffractometer D5005 (Siemens, Karlsruhe, Germany). Data were collected from 2θ=20-40° with a step size of 0.02° and a normalized count time of 1 s/step. The phase composition was checked by means of JCPDS reference patterns for α-TCP (PDF Ref 09-0348) and HA (PDF Ref 09-0432). Crystal sizes and quantitative phase compositions of the materials were calculated by means of total Riveted refinement analysis with the TOPAS software (Bruker A X S, Karlsruhe, Germany). As references the system internal database structures of α-TCP and HA were used together with a Chebychev forth order background model and a Cu $K_\alpha$ emission profile (TOPAS Tutorial Quantitative Analysis, Users Manual, Bruker AXS, Karlsruhe, 2001).

The injectability was measured as described previously.

The particle sizes of the starting α-TCP cement matrix and of the filler additives used are shown in Table 7 below. The α-TCP had a monomial particle size distribution with a median particle diameter of about 10 μm. Several fine powdered additives (DCPA; $TiO_2$, CC) with a median size of 0.5-1.1 μm were added as fillers to the α-TCP to obtain a bimodal particle size distribution.

TABLE 7

Particle sizes of powder components and zeta-potentials in contact with water and a 50 mM trisodium citrate solution

| Material | Ø $d_{50}$ [μm] | Zeta potential [mV] Water | Zeta potential [mV] 0.05 M $Na_3$citrate |
|---|---|---|---|
| a-TCP | 9.8422 | −19.4 ± 2.2 | −51.5 ± 1.0 |
| $CaCO_3$ | 0.7244 | −17.3 ± 1.6 | −52.8 ± 2.1 |
| DCPA | 1.1608 | −18.4 ± 1.9 | −50.1 ± 1.0 |
| $TiO_2$ | 0.5535 | −23.1 ± 2.9 | −46.9 ± 1.3 |

Surface charges of particles (zeta-potential) in pure water were found to be −17 to −23 mV, which were altered to values of −46 to −52 mV by using trisodium citrate as additive to the liquid cement phase.

The maximum powder to liquid ratio for obtaining a workable cement paste of unfilled α-TCP cement was 3.5 g/ml, independent of sodium citrate liquid phase additive. Sodium citrate did not significantly decrease the amount of mixing liquid in this case, however the paste became more susceptible to shear thinning compared to sodium phosphate solution only. In contrast, the use of fine sized filler additives combined with a high surface charge due to citrate adsorption strongly increased the maximum P:L to 4 g/ml (CC), 4.5 g/ml ($TiO_2$) and 5 g/ml (DCPA) at 23.1 wt % filler concentration. The observed decrease of cement viscosity increased the injectability of the cement pastes as shown in FIG. 2. Single component unfilled α-TCP cement was only marginally injectable with water (7%) (A) or sodium citrate containing (35%) solutions (B) at a P:L of 3.5 with a continuous increase of the injection force occurring after needle blockage. Only the combination of a high zeta-potential and a bimodal particle size distribution by adding the filler component (C; 23% CC, D; 23% $TiO_2$, E; 23% DCPA: B to E all 0.5 M $Na_3$citrate/2.5% $Na_2HPO_4$) resulted in fully injectable cements at this P:L with low applied injection forces of about 50-70N.

The influence of filler content and powder to liquid ratio on the injectability was investigated in more detail using DCPA as a filler. Injectability results are shown in Table 8 below. Cements were quantitatively injectable at a constant P:L of 3.5 g/ml for filler contents between 13-33 wt %.

TABLE 8

| DCPA (wt %)\ | Injectability [%] | | |
|---|---|---|---|
| P/L (g/ml) | 13% | 23% | 33% |
| 3.5 | 97.50% | 96.50% | 96.76% |
| 3.75 | 10.94% | 96.04% | 55.96% |
| 4.0 | 8.68% | 12.40% | 9.02% |

Wet compressive strengths of encompassed cements at P:L 3.5 and at maximum P:L are displayed in FIG. 3. Strengths of cements mixed at P:L 3.5 were found to be ~50 MPa for pure α-TCP, the use of DCPA or $TiO_2$ as filler did not significantly influence strength at a constant P:L, however the use of less liquid at a higher P:L for these two fillers increased strength to 62 MPa ($TiO_2$) and 89 MPa (DCPA). Pre-compaction of cement pastes with 9 MPa resulted, for both DCPA and $TiO_2$ as fillers, in a strong increase of compressive strengths as indicated in FIG. 4 dependent of the filler content. Compressive strengths of unfilled α-TCP were found to be 70 MPa after 7 d setting, which increased to more than 140 MPa for DCPA and 110 MPa for $TiO_2$ as fillers. Surprisingly, strengths for CC as filler were much lower at all P:Ls with values of 9-14 MPa and even pre-compaction increased strength to only 23-40 MPa.

C. Acidic Setting Cement

Cement Preparation

β-Tricalcium phosphate was prepared by heating a mixture of dicalcium phosphate anhydrous (DCPA, Baker) and calcium carbonate (CC, Merck) in a molar ratio of 2:1 up to 1050° C. for 24 h, followed by quenching to room temperature. The sintered cake was crushed with pestle and mortar and sieved until it passed through a 355 μm sieve. The material was ground in a ball mill to a medium particle size $d_{50}$ of 9.8 μm. Monocalcium phosphate monohydrate with a medium particle size $d_{50}$ of 23.3 μm was purchased from Baker and used as received. Both materials were mixed in equimolar amounts in a coffee grinder for approximately 20-30 s.

The invention is equally applicable to acidic setting cements. To demonstrate this, the injectability of the above cement using trisodium citrate as the liquid component was compared with the same cement using citric acid. The proportion of injected cement was determined from the mass of cement remaining in a syringe having a 1 mm bore needle after injecting at a force of 300 N. The results are shown in Table 9 below. Injectability is improved using increasing concentrations of citric acid. Sodium citrate has the opposite effect, with the cement being virtually impossible to inject at 1 M sodium citrate.

TABLE 9

Injectability of acidic setting cement solutions

| Additive | P:L | Proportion Injected (wt %) |
|---|---|---|
| 0.5 M Sodium citrate | 3.3 | 51 ± 11.0 |
| | 4.0 | 1.37 ± 0.2 |
| | 4.5 | NI |
| | 5.0 | NI |
| 1 M Sodium citrate | 3.3 | 1.6 ± 0.9 |
| | 4 | NI |
| | 4.5 | NI |
| | 5 | NI |

TABLE 9-continued

Injectability of acidic setting cement solutions

| Additive | P:L | Proportion Injected (wt %) |
|---|---|---|
| 0.5 M Citric acid | 3.3 | 23.6 ± 5.2 |
| | 4 | 2.1 ± 1.1 |
| | 4.5 | NI |
| | 5 | NI |
| 1 M Citric acid | 3.3 | 79.7 ± 1.5 |
| | 4 | 76.3 ± 12.5 |
| | 4.5 | 9.3 ± 0.9 |
| | 5 | NI |

NI = not injectable

Stability on Storage

Brushite (DCPD) forming calcium phosphate cements are resorbable bone replacement materials due to the higher solubility of brushite at pH 7.4 compared to hydroxyapatite (HA) in physiological conditions. Following immersion in aqueous media, the DCPD component in a brushite cement may, depending on conditions, be stable, disintegrate or dissolve and reprecipitate to hydroxyapatite (HA). Brushite is formed in calcium phosphate cements when the pH value of the paste <4.2 when acidic calcium phosphates or phosphoric acid is used as a cement reactant as indicated in Equations 1 to 3:

$$Ca_3(PO_4)_2+H_3PO_4+6H_2O \rightarrow 3\ CaHPO_4.2H_2O \quad (1)$$

$$Ca_3(PO_4)_2+Ca(H_2PO_4)_2.H_2O+7H_2O \rightarrow 4\ CaHPO_4.2H_2O \quad (2)$$

$$Ca_3(PO_4)_2+Ca(H_2PO_4)_2+8H_2O \rightarrow 4\ CaHPO_4.2H_2O \quad (3)$$

Because brushite cements have such a fast setting reaction (several times higher than HA cements), a low powder to liquid ratio and setting retardants have to be used to keep the cement paste workable over an adequate time period. Strengths reported in literature for Brushite forming cements are in the range between 1-24 MPa for compressive and 0.7-4.5 MPa for diametric tensile strengths. Generally, the strengths of cements formed with phosphoric acid used as a reactant (Equation 1), are lower than those obtained for powder mixtures of mono- and tri-calcium phosphates and water (Equations 2 and 3), probably because the setting reaction occurs less controllably. At the same time, concentrated acid solutions need to be used in order to obtain a full conversion of the TCP reactant to brushite, which in turn causes violent setting reactions and can cause problems because of the very low pH of the cement mix.

The inventors have discovered that the starting powder mixtures from β-TCP and monocalcium phosphate monohydrate/anhydrous (MCPM/A) lost their ability to set during storage over some days, despite being stored in sealed containers, which was subsequently found to be related to their conversion to monetize in a dry state during ageing. Storage stability is a vital criterion if these cements are to be used as medical products. Cements were prepared by mixing β-TCP and MCPM or MCPA, sealed under laboratory or dry argon atmospheres and stored at 80° C., room temperature or 6° C. Other parameters investigated were the mixing regime of cement components and the addition of retarding pyrophosphate and citrate salts as to the powder mixtures. The solid-state reaction was monitored by means of X-ray diffraction analysis and the setting and mechanical properties of the cement after powder ageing were investigated. Thus one aim was to identify factors important for controlling the long-term stability (shelf life) of this degradable cement system.

Materials and Methods

β-TCP was synthesized by heating a mixture of $CaCO_3$ (Merck, Darmstadt, Germany) and $CaHPO_4$ (Mallinckrodt Baker, Griesham, Germany) with an overall calcium to phosphate molar ratio (Ca:P) of 1.5 to 1050° C. for 24 h prior to quenching at room temperature in a desiccator. The product was verified as being phase pure highly crystalline β-TCP by X-ray diffraction. The resultant 'cake' was ground in a pestle and mortar and passed through a 355 μm sieve, subsequently 125 g of powder was milled using a planetary ball mill (PM400 Retsch, Germany) at 200 rpm in 500 ml agate jars, 4 agate balls (30 mm) for 1 h. Pyrophosphate ions were incorporated into the β-TCP structure by adjusting the CaP ratio of the starting powder mixture to 1.25 prior to sintering. To study the effect of mixing regime, cements were also prepared by mixing the components using less energy with mortar and pestle and by manually passing them together through a 355 μm sieve.

The cement mixtures (40 g respectively) were transferred into 100 ml polyethylene containers and sealed under normal laboratory atmosphere (~60% rh) or after evaporating in a desiccator for 1 h over silica gel and filling the containers with dry argon atmosphere. The sealed containers were stored in a desiccators at 6°, 22° and 80° C. for up to 21 d and the cement properties were determined immediately after manufacture (0 days) and after 1 d, 3 d, 7 d and 21 d storage.

Cement pastes were prepared in a similar manner to that described above, by mixing the cement powder with the appropriate amount of 200 mM trisodium citrate solution on a glass slab for 20 s at a powder to liquid ratio of 2.5 g/ml. The initial setting time was determined using the Gilmore needle technique. Samples for compressive testing with an aspect ratio of 2:1 were prepared and measured as previously described.

X-ray diffraction patterns of the dry cement powders were as described above and the phase compositions checked by means of the appropriate JCPDS reference patterns Storage Atmosphere After having discovered that cement stored in sealed containers under 'ambient' laboratory conditions no longer set after 7 days, the first step was to establish the reason. Total or surface reaction of the most soluble solid component (MCPA/D) to brushite was suspected. However XRD revealed that almost after 2 days at ambient conditions neither MCPM nor MCPA was detected in cement powders and crystalline monetize had formed. As 'ambient' laboratory temperature and humidity can vary considerably the effect of storage temperature and atmosphere were studied as shown in Table 10.

TABLE 10

| 2nd dry solid component | Atmosphere | Temperature [° C.] | initial setting time [min] after ageing 0 d | 1 d | 7 d | 21 d |
|---|---|---|---|---|---|---|
| MCPM | air | 22 | 2.0 | no setting | no setting | no setting |
| MCPM | air | 6 | | 3.8 | 3.8 | 8.0 |
| MCPM | argon | 22 | | 2.0 | 1.8 | 1.6 |
| MCPM | argon | 80 | | no setting | no setting | no setting |
| MCPA | air | 22 | 1.7 | no setting | no setting | no setting |
| MCPA | air | 6 | | 4.5 | 7.0 | no setting |

Reactant Phase

Since MCPM contains water of crystallization, attempts were made to eliminate water by using anhydrous MCPA in place of MCPM. Storing cement mixes made with MCPM in air at 6° C. initially appeared to prevent cement decomposition since setting time was unaffected. However, after 21 d setting time had shortened considerably from 28 min to ~8 min. No decrease in setting time was observed when MCPM containing cement was stored in argon after 21 d. However when temperature was increased to 80° C., no setting occurred after only 1 d. Replacing MCPM for MCPA did little to improve stability in air, since at 6° C. after 7 d setting times were considerably reduced and after 21 d no setting occurred.

The compressive strength of cements immediately after mixing was found to be 28 MPa for β-TCP/MCPM mixtures and 20 MPa for β-TCP/MCPA mixtures. Strength measurement of these cements aged in air at room temperature and in argon atmosphere at 80° C. was not possible since no cement setting occurred. In contrast, a lower storage temperature of 6° C. kept strength of β-TCP/MCPM cements nearly stable for up to 7 d, however after 21 d a strong decrease to 8.5 MPa was observed. β-TCP/MCPA cements remained stable for the first day followed by a subsequent lost of their strength and ability to set over 21 d storage. Stable β-TCP/MCPA cement mixtures were obtained in argon at room temperature without significant changes of cement strengths over 21 d storage.

Influence of Mixing Technique on Cement Stability

Having considered compositional and external factors the effect of particle size of β-TCP and the mixing regime of the components on the long term stability of the brushite cement mix was investigated. This was found to be a critical parameter since hand mixed cement mixes made with ball milled β-TCP were stable for up to 21 d at room temperature in air with compressive strengths of ~28 MPa (Table 11), whereas mechanically mixed cements did not set after only 1 d of storage, independent of using only hand ground β-TCP ($d_{50}$=16.6 μm) and MCPM ($d_{50}$=69.8 μm) or 1 h ball milled material ($d_{50}$=7.3 μm for β-TCP and 24.4 μm for MCPM).

TABLE 11

| Cement preparation and mixing technique | Compressive strength [MPa] (initial setting time in min) after ageing: after mixing | 1 d | 7 d | 21 d |
|---|---|---|---|---|
| β-TCP ground for 1 h in ball mill prior to mixing, cement mixed with coffee grinder for 1 min | 27.9 +/− 0.6 (2.0) | no setting | no setting | no setting |
| II-TCP crushed and sieved <355 iml, cement mixed with coffee grinde r for 1 min | 31.6 +/− 3.6 (2.0) | no setting | no setting | no setting |
| β-TCP ground for 1 h in ball mill prior to mixing, hand mixed by sieving several times | 28.5 +/− 0.4 (2.0) | 30.2 +/− 6.1 (2.0) | 27.3 +/− 8.0 (2.2n) | 28.0 +/− 5.6 (3.0) |

Influence of Solid Additives on Cement Stability

Since a reduction in setting time accompanied the conversion to monetize the effect of two known retardant ions was investigated when added in soluble form to the solid phase for mechanically mixed cements. While sodium citrate was already added to the liquid phase this was necessary since the reaction was too vigorous in its absence. Further addition of trisodium citrate (10 mol % of β-TCP component) had little effect on stability, whereas the addition of citric acid both increased compressive strength and resulted in a cement stable for 21 d at ambient conditions, yet strength decreased slightly after storage to 35 MPa compared to initial 49 MPa. Sodium pyrophosphate improved stability since after 21 d the cement mix still set however strength was reduced compared to unmodified cement (Table 12) and citric acid stabilized formulations even at high storage temperatures.

TABLE 12

| | Compressive strength [MPa] (initial setting time) after ageing | | | |
|---|---|---|---|---|
| Additive | after mixing | 1 d | 7 d | 21 d |
| 10 mol % trisodium citrate | 22.6 +/− 3.7 (2.8 min) | no setting | no setting | no setting |
| 10 mol % citric acid | 48.9 +/− 8.7 (4.3 min) | 47.6 +/− 9.5 (5.0 min) | 38.6 +/− 7.8 (4.5 min) | 35.0 +/− 2.4 (4.5 min) |
| calcium pyrophosphate containing β-TCP | 17.5 +/− 2.5 (3.5 min) | 19.9 +/− 3.2 (3.3 min) | 10.9 +/− 2.1 (6.5 min) | 11.9 +/− 2.7 (9.0 min) |

The parameters relevant for aging are the storage temperature, air moisture and the mixing regime of the cement components. A decrease in storage temperature reduced the conversion rate, however even at 6° C. this did not prevent the ageing of the cement powders and the formation of monetize. Other factors are also homogeneous mixing of the cement powders as well as a high specific surface area. Only those cements, which were mixed thoroughly and homogeneously from pre-ground β-TCP by means of the ball mill/coffee grinder ($d_{50}$ β-TCP=7.3 μm; $d_{50}$ MCPM=24.4 μm) showed a significant ageing effect, the less efficient, but a more gentle mixing method by repeated sieving of either the raw powders ($d_{50}$ β-TCP=16.6 μm, $d_{50}$ MCPM=69.8 μm) or the separately pre-ground powders prevented conversion to monetize.

The addition of retarding reactants, e.g. calcium pyrophosphate, tri-sodium citrate or citric acid was found to be another way for stabilizing the cements against ageing, even if the cement powders were stored under normal (humid) laboratory conditions. The compounds are known for retarding the setting reaction of brushite- or HA-forming cements by inhibiting crystal growth of the cement product. The use of pyrophosphate ions within the β-TCP matrix resulted in mostly stable cement mixtures, however compressive strength (11-19 MPa) were significantly lower than for the well stabilizing citric acid (compressive strength=35-49 MPa). A long term experiment with this cement indicated that it remained stable even after six months storage under normal laboratory conditions without loosing its ability to set. Interestingly, the use of trisodium citrate had no effect on cement stability compared to the free acid, despite having similar solubility in water. This fact could probably be explained by the different pH-values of both compounds. While citric acid leads to a very low pH value in the cement paste, the rather neutral trisodium salt is a strong buffer that shifts the pH more to the basic region. Recently the inventors have found that β-TCP/MCPM cement mixes made with citric acid usually have a pH between 1.5-2 during setting, while trisodium citrate resulted in a pH of 2.5-3, both measured with 500 mM solutions. Because of the very small amount of liquid within the cement powders (probably three orders of magnitude less than in a cement paste), the liquid phase will be saturated with both retarders such that this pH effect will be more pronounced than for the use of (non-saturated) 500 mM solutions.

The invention claimed is:

[1. A self setting calcium phosphate cement comprising:

(i) a powdered component selected from the group consisting of:

(a) calcium phosphate, dicalcium phosphate anhydrous, dicalcium phosphate dihydrate, α-tricalcium phosphate, tetracalcium phosphate, hydroxyapatite, octacalcium phosphate, substituted forms thereof, or mixtures thereof;

(b) a carbonate, silicate, nitrate, oxide, sulphate or salt of calcium, zirconium, aluminium, titanium or silicon, or mixtures thereof; and (c) mixtures of (a) and (b), said powdered component having an average particle size $d_{50}$ of less than 15 μm, and (ii) a calcium phosphate based powder selected from the group consisting of tetracalcium phosphate, α-tricalcium phosphate, hydroxyapatite, monocalcium phosphate monohydrate, monocalcium phosphate anhydrous and mixtures thereof, said powder having an average particle size $d_{50}$ greater than that of the powdered component, said powdered component and said calcium phosphate based powder being suspended in water containing a dissolved zeta potential increasing additive in an amount of from 0.1 to 2 Mol per liter of water and in sufficient quantity to increase the zeta potential of the suspended particles to at least −30 mV, and wherein the zeta potential increasing additive is chosen to be compatible with the setting pH of the same calcium phosphate cement without the zeta potential increasing additive.]

[2. A cement as claimed in claim 1, wherein the $d_{50}$ of the calcium phosphate based powder is from 1.5 to 10 times greater than the $d_{50}$ of the powdered component.]

[3. A cement as claimed in claim 1, wherein the zeta potential increasing additive is an oligocarboxylic acid compound selected from the group consisting of a group I meat salt, a group II metal salt, an ammonium salt, and a mixed salt.]

[4. A cement as claimed in claim 3, wherein the oligocarboxylic acid compound has two or three carboxyl groups.]

[5. A cement as claimed in claim 3 wherein the oligocarboxylic acid compound has one or more hydroxyl groups.]

[6. A cement as claimed in claim 3 wherein the oligocarboxylic acid compound is a salt of citric acid, tartaric acid or malic acid.]

[7. A cement as claimed in claim 6 wherein said salt is trisodium citrate, disodium malate or disodium tartrate.]

[8. A cement as claimed in claim 1, wherein the zeta potential increasing additive is in sufficient quantity to increase the zeta potential of the calcium phosphate particles to at least −40 and preferably at least −50 mV.]

[9. A cement as claimed in claim 1, wherein the zeta potential increasing additive is present in an amount of from 0.2 to 1 M per liter.]

[10. A cement as claimed in claim 1, wherein the powdered component has a $d_{50}$ of no more than 10 μm.]

[11. A cement as claimed in claim 1, wherein the calcium phosphate based powder has a $d_{50}$ of at least 3 μm.]

[12. A cement as claimed in claim 1, wherein the calcium phosphate based powder is mechanically activated.]

[13. A cement as claimed in claim 1, wherein the volume ratio of the calcium phosphate based powder to the powdered component is in the range of from 50:50 to 95:5.]

[14. A cement as claimed in claim 1, wherein the powdered component constitutes no more than 40% by volume of the calcium phosphate based powder.]

[15. A cement as claimed in claim 14, wherein the powdered component constitutes no more than 30% by volume of the calcium phosphate based powder.]

[16. A cement as claimed in claim 15, wherein the powdered component constitutes from 10 to 25% by volume of the calcium phosphate based powder.]

[17. A self setting calcium phosphate cement comprising:

(i) a powdered component, said powdered component having an average particle size $d_{50}$ of less than 15 μm, and (ii) a calcium phosphate based powder, said powder having an average particle size $d_{50}$ greater than that of the powdered component, said powdered component and said calcium phosphate based powder being suspended in water containing a dissolved zeta potential increasing additive in an amount of from 0.1 to 2 Mol per liter of water and in sufficient quantity to increase the zeta potential of the suspended particles to at least −30 mV, and wherein the zeta potential increasing additive is chosen to be compatible with the setting pH of the same calcium phosphate cement without the zeta potential increasing additive and wherein neither said powdered component nor said calcium phosphate based powder is β-tricalcium phosphate.]

[18. A self setting calcium phosphate cement comprising:

(i) a powdered component selected from the group consisting of:

(a) calcium phosphate, dicalcium phosphate anhydrous, dicalcium phosphate dihydrate, α-tricalcium phosphate, tetracalcium phosphate, hydroxyapatite, octacalcium phosphates, substituted forms thereof, or mixtures thereof;

(b) a carbonate, silicate, nitrate, oxides, sulphate or salt of calcium, zirconium, aluminium, titanium or silicon, or mixtures thereof; and (c)mixtures of (a) and (b), said powdered component having an average particle size $d_{50}$ of less than 15 μm, and (ii) a calcium phosphate based powder selected from the group consisting of tetracalcium phosphate, α-tricalcium phosphate, hydroxyapatite, monocalcium phosphate monohydrate, monocalcium phosphate anhydrous and mixtures thereof, said powder having an average particle size $d_{50}$ greater than that of the powdered component, said powdered component and said calcium phosphate based powder being suspended in water containing a dissolved zeta potential increasing additive in an amount of from 0.1 to 2 Mol per liter of water and in sufficient quantity to increase the zeta potential of the suspended particles to at least −30 mV, and wherein the zeta potential increasing additive is an oligocarboxylic acid compound selected from the group consisting of a group I or group II metal salt, an ammonium salt or a mixed salt.]

[19. A cement as claimed in claim 10, wherein the powdered component has a $d_{50}$ of no more than 5 μm.]

*20. A self-setting calcium phosphate cement comprising (a) a powdered component selected from the group consisting of tetracalcium phosphate, hydroxyapatite and α-tricalcium phosphate, said powdered component having an average particle size $d_{50}$ of less than 15 μm; (b) a calcium phosphate based powder selected from the group consisting of tetracalcium phosphate, hydroxyapatite, and α-tricalcium phosphate, said powder having average particle size $d_{50}$ greater than that of the powdered component; (c) sodium citrate; and (d) a liquid component,*

*Wherein when either the powdered component or the calcium phosphate based component is suspended in water containing sodium citrate at a concentration of 0.05 Mol per liter, the zeta potential of the suspended particles is at least −30 mV.*

* * * * *